(12) United States Patent
Li et al.

(10) Patent No.: US 7,427,597 B2
(45) Date of Patent: Sep. 23, 2008

(54) METHOD OF TREATING BRAIN TISSUE DAMAGES

(75) Inventors: Hung Li, Taipei (TW); Woei-Cherng Shyu, Taipei (TW); Shinn-Zong Lin, Hualien (TW)

(73) Assignee: Academia Sinica, Taipei (TW)

( * ) Notice: Subject to any disclaimer, the term of this patent is extended or adjusted under 35 U.S.C. 154(b) by 49 days.

(21) Appl. No.: 11/284,796

(22) Filed: Nov. 21, 2005

(65) Prior Publication Data

US 2007/0116677 A1   May 24, 2007

(51) Int. Cl.
*A61K 38/00* (2006.01)
*A01N 37/18* (2006.01)
*C07K 14/00* (2006.01)
*C07K 1/00* (2006.01)

(52) U.S. Cl. ............. 514/12; 514/2; 530/300; 530/350; 530/324

(58) Field of Classification Search .......... None
See application file for complete search history.

(56) References Cited

OTHER PUBLICATIONS

Fujita et al. 1999, Mol. Brain Res., 63, 316-24.*
Gasser et al. 2003, 85, 662-69.*

* cited by examiner

*Primary Examiner*—Olga N Chernyshev
(74) *Attorney, Agent, or Firm*—Occhiuti Rohlicek & Tsao LLP

(57) ABSTRACT

A method of treating brain tissue damage, including administering to a subject in need thereof an effective amount of secretoneurin. Disclosed are methods of promoting angiogenesis or neurogenesis in the brain of subject. Also disclosed are a method of homing of stem cells to the brain of a subject and a method of protecting a neuronal cell from cell death.

9 Claims, No Drawings

SEQUENCE LISTING

```
<160> NUMBER OF SEQ ID NOS: 1

<210> SEQ ID NO 1
<211> LENGTH: 33
<212> TYPE: PRT
<213> ORGANISM: Homo sapiens

<400> SEQUENCE: 1

Thr Asn Glu Ile Val Glu Glu Gln Tyr Thr Pro Gln Ser Leu Ala Thr
1               5                   10                  15

Leu Glu Ser Val Phe Gln Glu Leu Gly Lys Leu Thr Gly Pro Asn Asn
            20                  25                  30

Gln
```

METHOD OF TREATING BRAIN TISSUE DAMAGES

BACKGROUND

Brain tissue damage, resulting either from injuries or disorders (e.g., neurodegenerative and cerebrovascular diseases), is a leading cause of long-term disability. Due to their pluripotency, embryonic stem cells (ES cells) hold a great promise for treating brain tissue damage (Taguchi et al., 2004, J. Clin. Invest.; 114(3):330-338). However, ethical and logistical considerations have hampered their use (Barinaga, 2000, Science, 287(5457):1421-1422). Use of non-ES pluripotent cells has also been exploited. They include adult bone marrow mesenchymal stem cells or stromal cells (Sanchez-Ramos et al., 2000, Exp. Neurol., 164(2):247-256 and Woodbury et al., 2000, J. Neurosci. Res., 61(4):364-370) and umbilical cord blood cells (Galvin-Parton et al., 2003, Pediatr. Transplant. 2003; 7(2):83-85 and Ha et al., 2001 Neuroreport., 2(16): 3523-3527). Nonetheless, requirements for in vitro expansion and HLA-matching have limited clinical applications of these cells. Thus, there is a need for an alternative method of treating brain tissue damage.

SUMMARY

This invention is based, at least in part, on the discovery that brain tissue damage can be repaired by administration of secretoneurin.

Accordingly, one aspect of this invention features a method of treating brain tissue damage. The method includes administering to a subject in need thereof an effective amount of secretoneurin. The method can be used to treat brain tissue damage caused by a cerebral ischemia, e.g., stroke, or a neurodegenerative disease, e.g., Alzheimer's disease, epilepsy, Huntington's disease, Parkinson's disease, or Spinocerebellar disease. The method may further include administering to the subject an effective amount of stem cells. Suitable stem cells include hematopoietic stem cells, umbilical cord-derived mesenchymal stem cells, and stem cells that are c-kit$^+$ or CD34$^+$. Preferably, the stem cells are autologous to the subject. For example, the cells can be enriched from the blood or bone marrow from the subject.

"Treating" refers to administration of a compound or composition to a subject, who is suffering from or is at risk for developing brain tissue damage or a disorder causing such damage, with the purpose to cure, alleviate, relieve, remedy, prevent, or ameliorate the damage/disorder, the symptom of the damage/disorder, the disease state secondary to the damage/disorder, or the predisposition toward the damage/disorder. An "effective amount" refers to an amount of the compound or composition that is capable of producing a medically desirable result, e.g., as described above, in a treated subject. The treatment method can be performed alone or in conjunction with other drugs or therapies.

This invention also features a method of promoting cerebral angiogenesis in a subject. The method includes administering intracerebrally to a subject in need thereof an effective amount of secretoneurin. The method further includes measuring a level of cerebral angiogenesis in the subject before and after administering secretoneurin to confirm promotion of cerebral angiogenesis. The method can also include administering to the subject an effective amount of stem cells, such as those described above.

Also within the scope of this invention is a method of promoting neurogenesis in the brain of a subject. The method includes administering intracerebrally to a subject in need thereof an effective amount of secretoneurin. The method further includes measuring a level of neurogenesis in the brain of the subject before and after administering promotion to confirm promotion of neurogenesis. For this purpose, one can use standard neurological behavioral measurements including those described in the examples below. The method can also include administering to the subject an effective amount of stem cells, such as those mentioned above.

This invention further features a method of promoting homing of stem cells to the brain of a subject by administering intracerebrally to a subject in need thereof an effective amount of secretoneurin. Suitable stem cells include those described above.

A method of preserving a neuronal cell is also contemplated in this invention. The method of claim includes contacting the cell with secretoneurin.

The details of one or more embodiments of the invention are set forth in the description below. Other features, objects, and advantages of the invention will be apparent from the description and from the claims.

DETAILED DESCRIPTION

The present invention relates to treating brain tissue damage using secretoneurin). Secretoneurin, a 33-amino acid neuropeptide (TNEIVEEQYTPQSLATLESVFQELGKLT-GPNNQ: SEQ ID NO: 1), is derived from endoproteolytic processing of chromogranin/secretogranins (Cg/Sg) family protein. It is a abundant protein within large dense core vesicles in the endocrine tissue and nervous system (Kirchmair et al. 1993, Neuroscience, 53, 359-365; Saria et al., 1993, Neuroscience, 54, 1-4; Kähler et al., 1996, Eur. J. Pharmacol., 304, 135-139; Fischer-Colbrie et al., 1995, Prog. Neurobiol. 46, 49-70; and Cozzi et al., 1989, Neuroscience 28, 423-41.) As described in the examples below, secretoneurin unexpectedly enhanced the targeting of stem cells to injured brain, protected neurons from cell death, and promoted neurogenesis and angiogenesis in injured brain. Not only did it protect existing neurons or glial cells in the brain, it also facilitated neural regeneration to replace damaged neurons glial cells.

While many secretoneurin preparations can be used to practice this invention, highly purified secretoneurin is preferred. Examples include mammalian secretoneurin (e.g., human, mouse, and rat secretoneurins) or non-mammalian secretoneurin having substantially the same biological activity as mammalian secretoneurin. Naturally occurring secretoneurin, chemically synthesized secretoneurin, and genetically engineered secretoneurin all can be used. Secretoneurin obtained by chemical synthesis or genetic engineering may be that having the same amino acid sequence as naturally occurring secretoneurin or an functionally equivalent there of. A "functional equivalent" refers to a polypeptide derivatives of a naturally occurring secretoneurin (SEQ ID NO: 1), e.g., a protein having one or more point mutations, insertions, deletions, truncations, a fusion protein, or a combination thereof. It possesses one or more of the activities of secretoneurin, e.g., the ability to protect cells from cell death, to promote angiogenesis or neurogenesis, and to mobilize stem cells from bone marrow into the peripheral blood or into the brain. The term "secretoneurin" also covers chemically modified secretoneurin. Examples of chemically modified secretoneurin include secretoneurin subjected to conformational change, addition or deletion of a sugar chain. Once purified and tested by standard methods, secretoneurin can be administered to a subject as described below.

To practice the treatment method of this invention, one can administer secretoneurin via intracerebral injection. A sterile injectable composition (e.g., aqueous or oleaginous suspension) can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

A carrier in a pharmaceutical composition must be "acceptable" in the sense of being compatible with the active ingredient of the formulation (and preferably, capable of stabilizing it) and not deleterious to the subject to be treated. For example, solubilizing agents, such as cyclodextrins (which form specific, more soluble complexes with one or more of active compounds of the extract), can be utilized as pharmaceutical excipients for delivery of the active compounds. Examples of other carriers include colloidal silicon dioxide, magnesium stearate, cellulose, sodium lauryl sulfate, and D&C Yellow # 10.

Suitable in vitro assays can be used to preliminarily evaluate the efficacy of a secretoneurin preparation. For example, one can measure the neuroprotective effect of the preparation. More specifically, the preparation can be added to a suitable cell culture (e.g., a primary cortical cell culture of rat or mouse neuron-glial cells as described in Example 1 below) and the level of protection is determined. One then compares the level with a control level obtained in the absence of the preparation. If the level of interest is higher than the control, the preparation is identified as being active for treating brain tissue damage. One can also evaluate the efficacy of a secretoneurin preparation by examining the preparation's effects on cell death according to standard methods. For example, one can measure the level of a protein involved in cell-death (e.g., caspase). If the level is lower than that obtained in the absence of the preparation, the preparation is determined to be active.

The preparation can further be examined for its efficacy in mobilizing bone marrow-derived stem cells to the peripheral blood or the brain by an in vivo assay. For example, the preparation can be evaluated in an animal (e.g., a mouse or rat model). The level of mobilized stem cells in the peripheral blood or the brain is determined by standard methods.

The preparation can also be administered to an animal model having brain tissue damage or a disorder causing such damage. The therapeutic effects of the preparation are then evaluated according to standard methods (e.g., those described in Examples 2-8 below). To confirm efficacy in promoting cerebrovascular angiogenesis, one can examine the animal before and after the treatment by standard brain imaging techniques, such as computed tomography (CT), Doppler ultrasound imaging (DUI), magnetic resonance imaging (MRI), and proton magnetic resonance spectroscopy ($^1$H-MRS).

One can also measure the expression level of a neuronal marker, a vacular marker, a glial marker, a trophic factor, or a cell death-related protein in a sample (e.g., cerebrospinal fluid) obtained from the animal before or after administration of secretoneurin to confirm efficacy. The expression level can be determined at either the mRNA level or the protein level. Methods of measuring mRNA levels in a tissue sample or a body fluid are well known in the art. To measure mRNA levels, cells can be lysed and the levels of mRNA in the lysates, whether purified or not, can be determined by, e.g., hybridization assays (using detectably labeled gene-specific DNA or RNA probes) and quantitative or semi-quantitative RT-PCR (using appropriate gene-specific primers). Alternatively, quantitative or semi-quantitative in situ hybridization assays can be carried out on tissue sections or unlysed cell suspensions using detectably (e.g., fluorescent or enzyme) labeled DNA or RNA probes. Additional mRNA-quantifying methods include the RNA protection assay (RPA) method and the serial analysis of gene expression (SAGE) method, as well as array-based technologies.

Methods of measuring protein levels in a tissue sample or a body fluid are also well known in the art. Some of them employ antibodies (e.g., monoclonal or polyclonal antibodies) that bind specifically to a target protein. In such assays, the antibody itself or a secondary antibody that binds to it can be detectably labeled. Alternatively, the antibody can be conjugated with biotin. Its presence can be determined by detectably labeled avidin (a polypeptide that binds to biotin). Combinations of these approaches (including "multi-layer sandwich" assays) can be used to enhance the sensitivity of the methodologies. Some protein-measuring assays (e.g., ELISA or Western blot) can be applied to body fluids or to lysates of cells, and others (e.g., immunohistological methods or fluorescence flow cytometry) can be applied to histological sections or unlysed cell suspensions. Appropriate labels include radionuclides (e.g., $^{125}$I, $^{131}$I, $^{35}$S, $^3$H, or $^{32}$P) enzymes (e.g., alkaline phosphatase, horseradish peroxidase, luciferase, or β-glactosidase), fluorescent/luminescent agents (e.g., fluorescein, rhodamine, phycoerythrin, GFP, BFP, and Qdot™ nanoparticles supplied by the Quantum Dot Corporation, Palo Alto, Calif.). Other applicable methods include quantitative immunoprecipitation or complement fixation assays.

Based on the results from the assays described above, an appropriate dosage range and administration route can be determined. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.001-100 mg/kg. Dosage variations are necessary in view of the variety of compounds available and the different efficiencies of various routes of administration. The variations can be adjusted using standard empirical routines for optimization as is well understood in the art. In general, secretoneurin can be administered at 10 to 500 μg/day/kg body weight for 2-10 days; preferably, 20 to 200 μg/day/kg body weight for 3-8 day; and, more preferably, 50 to 100 μg/day/kg body weight for 4 to 6 days.

The treatment method of this invention optionally includes administering to a subject an effective amount of stem cells. Both heterologous and autologous stem cells can be used. In the former case, HLA-matching should be conducted to avoid or minimize host reactions. In the latter case, autologous cells are enriched and purified from a subject to be treated before the cells are introduced back to the subject.

In both cases, secretoneurin can be used as the active ingredient to mobilize hematopoietic stem cells (HSCs) out of bone marrow so as to increase the number of stem cells in the peripheral blood, which home to the brain (HSCs, once in the peripheral blood, are called peripheral blood stem cells or PBSC).

Other factors, such as granulocyte-colony stimulating factor (G-CSF), can also be used to mobilize HSCs. In one embodiment, PBSCs are obtained from a subject as follows: A subject is first administered G-CSF to mobilize HSCs from bone marrow into the peripheral blood. After this enriching step, peripheral blood are collected and PBSCs purified. To prepare PBSCs, G-CSF is administered at 10 to 200 µg/day/kg body weight for 2-10 days. The G-CSF can be administered to a subject via any suitable routes. Examples include injection subcutaneously, intramuscularly, and intraperitoneally. PBSCs are generally purified based on their physical and biochemical properties. For example, peripheral blood cells may be concentrated for hematopoietic stem cells by centrifugation, counter-current elutriation, selection with cell surface markers (e.g., CD34+ or stem cell related antibodies), or removal of lineage positive (committed) hematopoietic cells. Such methods are well known in the art. See e.g., U.S. Pat. Nos. 5,061,620; 5,087,570; 5,061,620; 4,714,680; 4,965,204; and 5,035,994. Details of using G-CSF to obtain greater than 90% purity of PBSCs can be found U.S. application Ser. No. 11/134,613.

Stem cells other than PBSC can be used as long as they possess the potential to differentiate into cells of vascular or neural-glial lineage. Methods of preparing and testing such cells are well-known in the art. Examples includes embryonic stem cells (Thomson et al., 1995, Proc. Natl. Acad. Sci. U.S.A. 92:7844-7844; 1996, Biol. Reprod. 55:254-259; Shamblott et al., 1998, Proc. Natl. Acad. Sci. U.S.A. 95:13726; and U.S. Pat. Nos. 6,921,632 and 6,875,607), bone marrow-derived mesenchymal stem cells (Tse, et al., 2000, Journal of the American Society of Hematology, vol. 96, No. 11; Woodbury et al., 2002, J. Neuroscience Res. 96:908-917; Sanchez-Ramos et al., 2000, Exp. Neurol., 164(2):247-256; Woodbury et al., 2000, J. Neurosci. Res., 61(4):364-370; and U.S. Pat. Nos. 5,486,359, 6,355,239), and umbilical cord-derived stem cells (Mitchell et al., 2003, Stem Cells. 2003;21(1):50-60; Galvin-Parton et al., 2003, Pediatr. Transplant. 2003;7(2):83-85; Ha et al., 2001 Neuroreport., 2(16):3523-3527; and U.S. Provisional Application No. 60/706,377.

Purified stem cells are tested and stored by standard techniques. They can be administered intracerebrally to a subject in need thereof. In general, $1 \times 10^4$ and $1 \times 10^6$ (e.g., $5 \times 10^4$ to $8 \times 10^6$ and more preferably $1 \times 10^5$ to $6 \times 10^5$) cells are administered. Multiple sites can be used depending on the site and nature of particular damage. Examples below describes approximate coordinates for administering cells in a rat or a mouse. Coordinates for other disorders in other species can be determined accordingly based on comparative anatomy. Before or after the treatment, a subject can be examined to confirm treatment efficacy. To this end, one can use suitable standard tests or techniques described above and in the examples below.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

EXAMPLE 1

Neuroprotective effects of secretoneurin (SN) were evaluated in vitro. Primary cortical cells were prepared from the cerebral cortex of gestation day 17 embryos from Sprague-Dawley rats as described in Murphy et al., 1990, FASEB J. 4, 1624-33. Four days later, the cell cultures were replenished with minimum essential medium (MEM, GIBCO-BRL) containing 0.5 g/L BSA and N-2 supplement, $0.5 \times 10^{-3}$ mol/L pyruvate and antibiotics. Finally, the culture medium was changed to serum-free MEM containing $1 \times 10^{-3}$ mol/L pyruvate, $1 \times 10^{-3}$ mol/L glutamate, 0.5 g/L BSA, $0.3 \times 10^{-3}$ mol/L KCl, and antibiotics on the seventh day.

The primary cortical neuron cultures were prepared seeded in 24-well plates and pre-treated with 1 µg/L SN (Neosystems, Strasbourg, France). After 20 minutes, $H_2O_2$ ($10^{-5}$ or $10^{-4}$ mol/L) was added to the medium. After an incubation for 24 hours, the culture media were collected for lactate dehydrogenase (LDH) activity assays as described in Koh et al., 1987, J. Neurosci. Methods 20, 83-90. LDH activity was then measured in cultures incubated with or without SN treatment.

It was found that treatment with SN (1 µg/mL) prior to $H_2O_2$ incubation significantly reduced LDH activity in cultures exposed to $H_2O_2$ in comparison with the control.

To analyze the effect of SN on neuronal survival under $H_2O_2$ toxic conditions, cells positive for MAP (a neuronal marker) were quantified. Briefly, the primary cortical cell cultures were washed with PBS and fixed with 1% paraformaldehyde. Immunostaining procedure with specific antibody against MAP-2 (1:1000, BM) and quantification of MAP-2+ cell were performed according to the methods described in Wang et al., 2001, Stroke 32, 2170-8 (2001).

It was found that SN (1 µg/mL) pre-treatment significantly increased the of density MAP-2+ cells in primary cortical neuron cultures as compared with vehicle control.

To examine antiapoptotic effect of SN on primary cortical cultures, caspase-3 activity and capase-3 immunohistochemistry analysis were performed. Primary cortical neuron cultures were obtained in the manner described above, incubated with 10 µg/L SN, and treated with $10^{-5}$ mol/L $H_2O_2$ for 24 hours. Fluorometric assays of caspase-3 activity were performed using commercial kits (Bio-Rad) following the manufacturer's instruction. Immunofluorescent staining of activated caspase-3 in the primary cortical neuron cultures were conducted using primary antibody against active fragment of caspase-3 (R & D Systems) according to the method described in Niquet et al., 2003, Proc. Natl. Acad. Sci. U S A 100, 2825-30. The results showed that SN-treated primary cortical cells had significantly lower caspase-3 activity than control cells.

To investigate the molecular mechanism of SN's antiapoptotic effect, western blot analysis was conducted to examine expression of apoptosis-related proteins, such as phosphorylated Stat-3, ERK1/2, p38, JNK, Akt, Bcl-2, Bcl-xL, Bax, and Bad.

Briefly, the above-described primary cortical cells were incubated with SN (10 µg/L) for different time durations (0.5 hour, 1 hour, 3 hours, 8 hours, and 12 hours) before they were lysed in a buffer containing 320 mM sucrose, 5 mM HEPES, 1 µg/ml leupeptin, 1 µg/ml aprotinin. The resulting cell lysates were centrifuged at 13,000 g for 15 minutes. The pellet was resuspended in a sample buffer (62.5 mM Tris-HCl, 10% glycerol, 2% SDS, 0.1% bromophenol blue, and 50 mM DTT) and subjected to SDS-polyacrylamide gel (4-12%) electrophoresis. The gel was transferred to a Hybond-P nylon membrane and followed by incubation with appropriately diluted antibodies to p-ERK1/2 (dilution 1:200; Santa- Crutz), p-p38 (dilution 1:200; Santa-Crutz), p-JNK (dilution 1:200; Santa-Crutz), p-Akt (dilution 1:200; Calbiochem), p-Stat-3 (dilution 1:200; Santa-Crutz), Bcl-2 (dilution 1:200; Santa-Crutz), Bcl-xL (dilution 1:200; Transduction Laboratories), Bax (dilution 1:200; Santa-Crutz), Bad (dilution 1:200; Transduction Laboratories) and β-Actin (dilution 1:2000, Santa-Crutz). Specific p-ERK1/2 pathway inhibitor PD98059 (10 μM) (Cell Signaling Technology) and p-Akt pathway inhibitor wortmannin or LY294002 (10 nM, Calbiochem) were applied to the primary cortical culture to suppress enzyme binding in order to block the transcriptional signal of p-ERK1/2 and p-Akt. Membrane blocking, primary and secondary antibody incubations, and chemiluminescence reactions were conducted for each antibody according to the manufacturer's protocol. The intensity of each band was quantified by a Kodak Digital Science 1D Image Analysis System (Eastman Kodak, Rochester, N.Y.).

Gelatin zymographic analysis was also conducted. Briefly, primary cortical culture was developed as above in the presence of SN (5 μg/L), PD98059 (5 μM) and wortmannin (50 nM). Zymographic analysis was performed as described in Gursoy-Ozdemir et al., 2004, J Clin Invest 113, 1447-55.

It was found that expression levels of various anti-apoptotic proteins such as Bcl-2 were reduced in primary cortical neurons were treated with $H_2O_2$, and this reduction was considerably inhibited by SN pretreatment. It was also found that the expression of activated Akt and ERK1/2 increase one hour after SN treatment in a time-dependent manner. At this time the ratio of p-Akt and p-ERK1/2/Actin protein reached a peak level of about a two-fold increase in treated cells compared with the control cells. The expression levels of p38 and JNK showed no statistically significant differences between treated and control cells. However, it was found that, following the addition of the specific inhibitor of activated Akt (LY294002) and activated ERK1/2 (PD98059) to $10^{-4}$ mol/mL $H_2O_2$-treated cells, SN (1 μg/mL) could not increased MAP-2 immunreactive cell density in primary cortical neuron cultures as compared with vehicle control.

EXAMPLE 2

Neuroprotective effects of SN were studied in vivo. To induce ischemia, adult male Sprague-Dawley rats (each weighing more than 300 g) were anesthetized with chloral hydrate (0.4 g/kg, ip) and subjected to right middle cerebral artery (MCA) ligation and bilateral common carotid artery (CCAs) clamping according to the method described in Chen et al., 1986, Stroke 17, 738-43 (1986). The rats were divided into two groups, SN and Control groups, ten in each. 30 minutes after MCA ligation, each of the rats in the SN group was injected intracerebrally with recombinant human SN (4 μg in 4 μl) (ProSpec-Tany TechnoGene, Israel), each in the Control group was injected with vehicle (4 μl, PBS) through a 26-gauge Hamilton syringe (Hamilton Company, Reno, Nev.). The SN or vehicle was injected into 3 cortical areas adjacent to the right MCA, 3.0 to 5.0 mm below the dura. The approximate coordinates for these sites were 1.0 to 2.0 mm anterior to the bregma and 2.5 to 3.0 mm lateral to the midline, 0.5 to 1.5 mm posterior to the bregma and 3.5 to 4.0 mm lateral to the midline, and 3.0 to 4.0 mm posterior to the bregma and 4.5 to 5.0 mm lateral to the midline. After 90 minutes of ischemia, the 10-O suture on the MCA and arterial clips on CCAs were removed to allow reperfusion.

Behavioral assessments were performed 3 days before cerebral ischemia, and 72 hours after cerebral ischemia. The tests measured (a) body asymmetry and (b) locomotor activity (Chang et al., 2003, Stroke 34, 558-64). It was found that rats in the SN group exhibited significantly reduced body asymmetry in comparison to that of controls three days after cerebral ischemia. The measured locomotor activity such as vertical activity, vertical movement time, and number of vertical movements significantly were high in these rats receiving SN treatment than the control rats.

Further, grip strength was analyzed using Grip Strength Meter (TSE-Systems, Germany) according to a method modified from that described in Dunnett et al., 1998, Neurosci Lett 246, 1-4. In brief, grip strength ration was measured on each forelimb separately and was calculated as the ratio between the mean strength out of 20 pulls of the side contralateral to the ischemia and that of ipsilateral side. In addition, the ratio of grip strength post-treament and baseline were also calculated and changes were present as a percentage of baseline value.

Furthermore, measurement of grip strength was performed to examine the forelimbs strength for all experimental rats at the time of baseline and 28 days after each of the three treatments. The final results revealed that higher ratio of grip strength was found in the SN group in comparison with the rats in the control group.

Effects of SN on reducing infarction volumes were examined. Cerebral ischemia was induced in 16 rats in the same manner described above. 30 minutes later, eight of the rats received SN, and the other received saline. Three days later, each rat was euthanized, perfused intracardially with saline, subjected to TTC staining by a standard method (Wang et al., 2001, Stroke 32, 2170-8). To minimize artifacts induced by post-ischemic edema in the infarcted tissue, the volume of infarction was also calculated by a method modified from that described in Lin. et al, 1993, Stroke 24, 117-21.

It was found that the SN-treated rats and saline-treated controls had average total infarction volumes of $73 \pm 17$ mm$^3$ and $182 \pm 16$ mm$^3$, respectively. The largest infarction area in the two groups were $9.4 \pm 3.3$ mm$^2$ and $19.7 \pm 2.9$ mm$^2$, respectively. Infarcted slices were also significantly different, with $6.7 \pm 0.4$ slices/rat in control and $3.1 \pm 0.5$ slices/rat in SN treated rats.

Seven SN treated rats and seven-saline treated rats also had their physiological parameters measured. No difference was found in systemic blood pressure, blood gases, blood glucose, or serum electrolyte levels, suggesting that SN does not influence physiological parameters.

The above results suggest that intracerebral SN administration improves neurological behavior and reduces infarct volume after cerebral infarction caused by cerebral ischemia.

EXAMPLE 3

The neuroprotective effects of SN were verified by immunostaining of neuron-specific proteins Neu-N and MAP-2. It was found that the number of cells positive for MAP-2 and Neu-N in the penumbric region surrounding the ischemic cores was significantly higher in SN-treated rats than in vehicle-treated rats.

It is known that caspase-3 can be activated by cerebral ischemia. To study the neuroprotective mechanism of SN, 6 SN-treated rats and 6 control rats were euthanized 8 hours after MCA ligation, perfused with 4% paraformaldehyde, and subjected to caspase-3 immunoreactivity tests. Slices were prepared from the rats by standard procedures and were incubated with primary antibody against caspase-3 (cleaved caspase-3 antibody, D175, dilution 1:500; Cell Signaling) conjugated with Cy3 (1:500, Jackson Immunoresearch) for 20 hours at 4° C., washed 3 times with PBS, and then observed with fluorescent microscopy (Carl Zeiss, Axiovert 200M). The extent of apoptosis was measured as the number of caspase-3+ apoptotic cells per mm². In addition, apoptosis-related protein was also examined in the SN-treated and control rats using Western blot analysis (Harada. et al. 2005, Nat. Med. 11, 305-11).

It was found that the penumbra surrounding the ischemic cores in SN-treated rats contained few cells expressing activated caspase-3 than in control rats. It was also found that SN-treated rats had significantly more expression of antiapoptotic protein such as Bcl-2 and Bcl-xL than the control rats.

The above results suggest that SN protect against apoptosis in cerebral ischemia by inhibiting activation of caspase-3 and upregulating of anti-apoptotic protein, e.g., Bcl-2 and Bcl-xL.

EXAMPLE 4

To determine whether stem cells homed into the injured brain tissue upon SN treatment, Bromodeoxyuridine (BrdU) labeling was used to follow the engraftment of HSCs to the brain seven days after cerebral ischemia.

BrdU, a thymidine analog, can be incorporated into DNA of dividing cells during S-phase and therefore was used for mitotic labeling (Sigma Chemical, MO). Rats were induced to develop cerebral ischemia in the manner described above, injected with BrdU, and sacrificed three to seven days latter. They then were subjected to BrdU staining using specific anti-BrdU antibody (1:400, Mannheim, Germany) and quantification by a standard method (Zhang et al., 2001, Neuroscience 105, 33-41). Cumulative BrdU labeling revealed a few BrdU immunoreactive cells in the ipsilateral cortex near the infarcted boundary and subventricular region of ischemic hemisphere. BrdU immunoreactive cells were also found around the lumen of varying calibers of blood vessels in the perivascular portion of the ischemic hemisphere. BrdU pulse labeling experiments were also conducted. It was found that BrdU immunoreactive cells significantly increased in SN treated rats (n=8) compared with those of saline control rats (n=8).

The above results suggest that HSCs are involved and that SN induces stem cells mobilization/homing to the ischemic brain.

EXAMPLE 5

Double staining immunohistochemistry was performed on brain slices from SN treated rats and control rats to determine whether mobilizing HSCs differentiated into neuronal and glial cells at ischemic site.

To identify the expression of cell type-specific markers in BrdU+ cells, double immunofluorescence staining was performed to test for the expression of glial fibrillary acidic protein (GFAP), von Willebrand factor (vWF), microtubule-associated protein 2 (MAP-2), and neuronal nuclei (Neu-N). A standard method was used to perform immunofluorescence staining with specific antibodies against BrdU (1:400, Mannheim, Germany) conjugated with FITC (1:500, Jackson Immunoresearch) or Cy3 (1:500, Jackson Immunoresearch), GFAP (1:400, Sigma) with Cy3 (1:500, Jackson Immunoresearch), MAP-2 (1:200, BM) with Cy3, Nestin (1:400, Sigma) with FITC, Neu-N (1:200, Chemicon) with FITC, vWF (1:400, Sigma) with Cy3, CXCR4 (CD 184, 1:100, Torrey Pines Biolab) with Cy3 and Doublecortin (Dcx, 1:100, Santa Cruz Biotechnology) with Cy3 (Li, et al., 2002, Neurology 59, 514-23).

The tissue sections were analyzed with a Carl Zeiss LSM510 laser-scanning confocal microscope. The result showed some BrdU+ cells colocalized with GFAP, Neu-N, and MAP-2 in brains slices from SN treated rats. SN-treated rats also had more BrdU+ cells co-expressing the neuronal phenotypes of GFAP+, Neu-N+ and MAP-2+ cells in ischemic cortical areas than the saline-treated rats.

To study homing and migration of stem cells, doubling immunofluorescence of specific markers for CXCR4 and Dcx was also performed. It was found that a major part of the penumbric region expressed specific phenotype marker of CXCR4, which was colocalized with BrdU immunostaining. The marker of Dcx was also found surrounding the ischemic region in double immunostaining assay.

The above results suggest that SN enhances neurogenesis in vivo and that engrafted stem cells migrate to home onto the penumbra area for reparing the injured brain.

EXAMPLE 6

Double immunohistochemistry staining, FITC-dextran perfusion, and blood vessel density assay were performed to demonstrate whether SN induces angiogenesis through homing HSCs differentiated into vascular-endothelial cells at ischemic sites.

In order to examine the blood vessels, rats were intravenously administered with fluorescent plasma marker (FITC-dextran, Sigma). The cerebral microcirculation in each rat was observed using fluorescent microscopy (Carl Zeiss, Axiovert 200M), according to the method described in Morris et al., 1999, Brain Res. Brain Res. Protoc. 4, 185-91. To quantify the cerebral blood vessel density and examine the vascular remodeling by macrophage, each rat was anesthetized with chloral hydrate and perfused with 4% paraformaldehyde. Histological sections (6 μm) were obtained and stained with specific antibody to CD-31 (1:100, BD Pharmingen), OX-42 (1:400, Serotec), ED-1 (1:500, Serotec) and conjugated with Cy-3 (1:500, Jackson Immunoresearch PA USA). The number of blood vessels was determined by the method described in Taguchi et al., 2004, J. Clin. Invest. 114, 330-8.

The result indicated that several BrdU+ cells showing vascular phenotypes (vWF+ cells). They were found around the perivascular and endothelial regions of the ischemic hemispheres of SN-treated rats. Also, treatment with SN (n=6) significantly enhanced cerebral microvascular perfusion with FITC-dextran in comparison to control ones (n=6). Quantitative measurement of blood vessel density examined by CD31 immunoreactivity showed that ischemic rats treated with SN (n=6) had significantly more neovasculatures in the penumbric area than the control (n=6).

To demonstrate the association between angiogenesis and macrophage/microglial (MA/MI), total number of positive MA/MI per section was counted according to the method described Pipp et al., 2003, Circ. Res. 92, 378-85. The results indicate several cells expressed MA/MI phenotypes (OX-42/ED-1 cells) and infiltrated around the perivascular regions (FITC-dextran perfused vessels) of the ischemic hemispheres of SN-treated rats. The SN-treated rats had significantly more MA/MI around the vessels than the control rats.

In addition, protein expression of β1-integrin was also studied by Western blotting analysis using specific antibody against β1-integrin (Chemicon). To see if β1-integrin activation was blocked by a synthetic cyclic RGD peptide, the peptide (1 μg/ml, Chemicon) was added to the SN before being injected into the ischemic brain. Infarction volume analysis by TTC staining and neurological behavioral measurement were also conducted in the manner described above.

It was found that the SN treated rats (n=4) had higher expression level that the control rats (n=4). However, after adding the synthetic cyclic RGD peptide, the two groups of rats showed no significant difference in β1-integrin expression or infarcted size. The above results demonstrate that SN induced angiogenesis and vascular remodeling and that the inducement involved stem cell-derived macrophage/microglial (MA/MI) and β1-integrin.

EXAMPLE 7

An increased vessels density would enhance neuronal survival, especially associated with an increased cerebral blood flow (rCBF), which resulted in efficient delivery of oxygen and nutrient. To examine the rCBF in the ischemic brain, the above-described experimental rats were received diamox injection and monitored by laser doppler flowmetry (LDF) under anesthesia after cerebral ischemia.

Each rat was positioned in a stereotaxic frame and baseline local cortical blood flow (bCBF) was measured every day for 5 days after cerebral ischemia with a laser doppler flowmeter (LDF monitor, Moore Instructment England) in anesthetized state (chloral hydrate) as previously described with modification (Tuettenberg et al., 2001, Neurosci Lett 315, 65-8). The rCBF was examined after intraperitoneal injection of 50 mg/kg acetazolamide (Diamox, Lederle) and defined as percentage changes of bCBF.

It was found that SN-treated rats had significant increase in rCBF of the MCA cortex of ischemic brain (n=6) than the control rats (n=6). The results suggest that SN facilitates rCBF in the ischemic brain.

EXAMPLE 8

It was known that c-kit receptor-mediated pathway plays an important role in stem cells mobilization/homing. To address the cellular mechanism of SN-induced stem cells mobilization/homing, adult male c-kit mutant mice (W/W$^v$) and their normal littermates (NL) (weight>30 g) were induced to develop cerebral ischemia and further examined.

WBReJ W/+ and C57BL/6 W$^v$/+ mice were purchased from the Jackson Laboratory. Colonies were maintained by brother-sister mating of heterozygous animals. W/+ adults have a moderate-sized white belly spot, white feet, and a white tipped tail. The change of C to T at position 2007 of the c-kit gene creates an NsiI site that was used to identify the W$^v$ allele mutation (Yoshinaga et al., 1991, Development 113, 689-99). Adult male c-kit mutant mice (W/W$^v$) and their normal littermates were anesthetized with chloral hydrate (0.3 g/kg, ip) and subjected to right middle cerebral artery (MCA) ligation and bilateral common carotid artery (CCAs) clamping (Chen et al., 1986, Stroke 17, 738-43). 15 minutes after MCA ligation, the mice were injected intracerebrally with recombinant human SN (2 μg in 4 μl PBS ) (Neosystems, Strasbourg, France) or vehicle (4 μl of PBS) through a 26-gauge Hamilton syringe (Hamilton Company, Reno, Nev.) into three cortical areas adjacent to the right MCA, 1.0 to 2.0 mm below the dura as mentioned above. The approximate coordinates for these sites were 0.5 to 1.0 mm anterior to the bregma and 1.0 to 2.0 mm lateral to the midline, 0 to 0.5 mm posterior to the bregma and 1.5 to 2.0 mm lateral to the midline, and 1.0 to 2.0 mm posterior to the bregma and 2.5 to 3.0 mm lateral to the midline. After 60 minutes of ischemia, the 10-O sutures on the MCA and arterial clips on CCAs were removed to allow reperfusion. Then, cumulative labeling of BrdU was conducted for 5 days. The BrdU immunostaining and quantification were described above.

The results showed that many BrdU immunoreactive cells scattered over penumbric area, subventricular zone, hippocampus, and peri-vascular area in SN-treated NL mice. In contrast, few BrdU immunoreactive cells were found in the W/W$^v$ mice. In quantitative analysis, BrdU immunoreactive cells significantly increased in SN-treated NL mice (n=6) compared with those of W/W$^v$ mice (n=6).

In addition, each mouse was subjected to H&E staining and its infarcted volume was measured. It was found that the average infarcted volume of SN treated NL mice was significantly smaller that that of the W/W$^v$ mice. The results demonstrate that SN promote stem cells mobilization/homing to ischemic tissues via a c-kit receptor-mediated pathway.

All measurements in the above examples were performed blindly. Results were expressed as mean±SEM. The behavioral scores were evaluated for normality. Student's t-tests were used to evaluate mean differences between the control and the SN-treated group.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of treating brain tissue damage, comprising administering to a subject in need thereof an effective amount of secretoneurin, wherein the secretoneurin is administered intracerebrally into an affected area and the brain tissue damage is caused by cerebral ischemia or stroke.

2. The method of claim 1, wherein the brain tissue damage is caused by cerebral ischemia.

3. The method of claim 1, wherein the brain tissue damage is caused by stroke.

4. A method of promoting cerebral angiogenesis in a subject suffering from cerebral ischemia or stroke, comprising administering to the subject an effective amount of secretoneurin, wherein the secretoneurin is administered intracerebrally into an affected area.

5. The method of claim 4, wherein the subject suffers from stroke.

6. The method of claim 4, wherein the subject suffers from cerebral ischemia.

7. A method of promoting neuronal survival in the brain of a subject suffering from cerebral ischemia or stroke, comprising administering to the subject an effective amount of secretoneurin, wherein the secretoneurin is administered intracerebrally into an affected area.

8. The method of claim 7, wherein the subject suffers from stroke.

9. The method of claim 7, wherein the subject suffers from cerebral ischemia.

* * * * *